United States Patent [19]

Citri

[11] Patent Number: 5,344,761
[45] Date of Patent: Sep. 6, 1994

[54] DEVICE FOR SOLID PHASE BACTERIOLOGICAL TESTING CONTAINING TEST AREAS FORMED BY LINES OF AN ANTIBACTERIAL COMPOSITION

[75] Inventor: Nathan Citri, Jerusalem, Israel

[73] Assignee: Yissum Research Development Company of the Hebrew University of Jerusalem, Jerusalem, Israel

[21] Appl. No.: 909,788

[22] Filed: Jul. 7, 1992

[51] Int. Cl.$^5$ .......................... C12Q 1/02; C12Q 1/04; C12N 11/12; C12M 1/20

[52] U.S. Cl. ........................................ 435/29; 435/32; 435/34; 435/178; 435/179; 435/299; 435/300; 435/301; 435/805

[58] Field of Search ................. 435/29, 32, 34, 174, 435/178, 179, 180, 293, 297, 299, 300, 301, 805

[56] References Cited

U.S. PATENT DOCUMENTS

| | | | |
|---|---|---|---|
| 3,715,280 | 2/1973 | Farmer | 435/301 X |
| 3,838,012 | 9/1974 | Higgens et al. | 435/301 |
| 3,929,583 | 12/1975 | Sharpe et al. | 435/301 |
| 4,255,522 | 3/1981 | Fusenig et al. | 435/297 |
| 4,288,543 | 9/1981 | Sielaff et al. | 435/34 |
| 4,381,343 | 4/1983 | Citri | 435/24 |

*Primary Examiner*—David M. Naff
*Attorney, Agent, or Firm*—Darby & Darby

[57] ABSTRACT

A device for solid phase bacteriological testing is provided having an absorbent solid support surface for bacterial culture subdivided into a multiplicity of individual adjacent test areas with lines of an antibacterial composition. The lines may intersect to form a grid may be parallel to form parallel channels, and may be on a sheet of bibulous cellulose which can be impregnated with a bacterial culture. The composition is preferably water-soluble and in the form of an ink containing an aniline dye such as Brilliant Green that is inhibitory to bacteria. The support surface can include a bacterial growth medium or may be supported on a solidifying bacterial growth medium, and the medium may contain agar-agar.

7 Claims, 1 Drawing Sheet

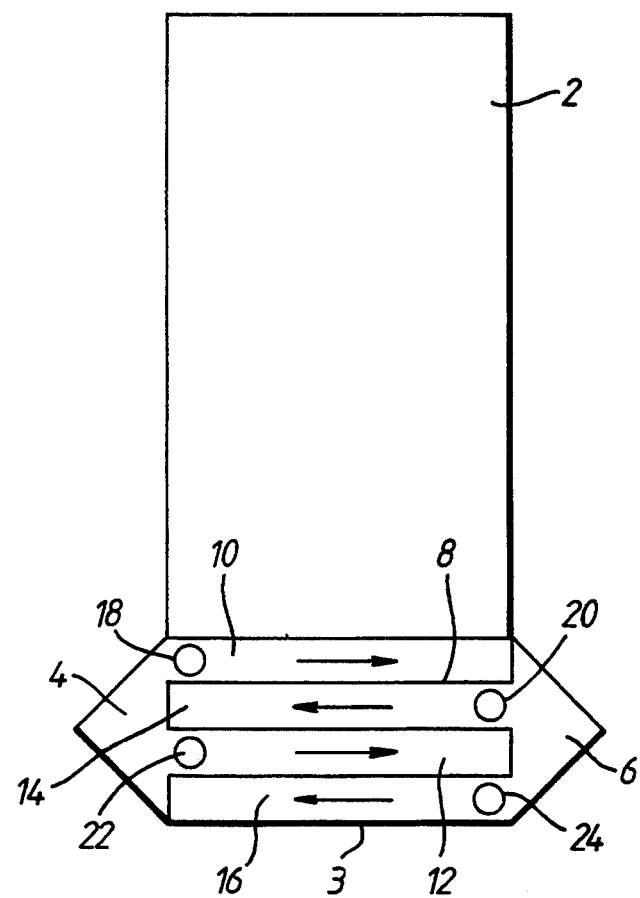

DEVICE FOR SOLID PHASE BACTERIOLOGICAL TESTING CONTAINING TEST AREAS FORMED BY LINES OF AN ANTIBACTERIAL COMPOSITION

BACKGROUND OF THE INVENTION

1. Field of the Invention

The present invention relates to a solid support for bacterial culture. More particularly the present invention relates to an improved device for carrying out microbiological assays and related procedures utilizing solid growth media.

2. Description of the Prior Art

Solid growth media for cultivating bacteria have been used in diagnostics for over 100 years. The various applications included identification of causative infectious agents, based on the appearances of discreet colonies on differential and selective media, containing, where applicable, reagents and color indicators facilitating biochemical characterization. Similarly, the susceptibility of an infecting agent to a variety of antibacterial agents could be assessed.

A reversal of procedure, namely the use of a bacterial strain susceptible to any such agent enables the detection of the presence of that agent in an unknown sample. Several tests based on this principle are currently used to detect antibacterials in milk, food or in other substances of interest.

Similarly, appropriate bacterial strains and media can be applied to the detection of growth promoting agents or of agents otherwise affecting the growth or the biosynthetic, metabolic or enzymatic activities of the bacterial test strain.

The classical format of such "solid-phase" microbiological or bacteriological assays is the Petri dish containing agar based growth medium. Agar-agar, which is the most commonly used solidfying agent can be replaced with silica or gelatin or other gelling substances. Alternatively, absorbent materials, such as bibulous cellulose in the form of filter paper or cardboard or any other absorbent can be cut as desired and impregnated with liquid growth medium. The solidified, as well as the impregnating, growth medium may take the shape of the Petri dish or any other shape required, to provide the desired solid base for the assay.

The main advantages of solid base bacteriological assays are simplicity and economy. The economy is further increased by increasing the number of tests per area of the test plate. A single Petri dish can be subdivided to provide for more than one test. However, interference between adjacent test areas is often observed if more than 4–6 samples are applied to one dish. This is a major limitation to the use of the classical format in large-scale screening.

A partial solution has been provided by redesigning the format so as to accommodate more samples per area unit. For example, the Petri dish can be replaced with a tray subdivided to resemble a diminutive ice-cube tray. The resulting compartments are physically separated and each can accommodate one sample. This format is used by Gist-Brocades in their screening test (Delvotest) for antibiotics in milk.

SUMMARY OF THE INVENTION

The primary object of the present invention is to allow a similar or greater increase in density of testing areas without requiring any structural barriers. Thus, according to the present invention, no replacement of the standard Petri dish is needed and no new design of any equipment is necessary. In fact, the present invention can be applied to any form or shape of a solid assay and is not subject to limitations inherent to the design or modification of bacteriological culture ware, disposable or reusable.

The principle of the present invention is based on the provision of chemical, rather than structural, barriers for creating multiple test areas.

Thus, according to the present invention there is now provided a solid support for bacterial culture of the type having an absorbent testing surface for solid phase bacteriological testing, comprising a plurality of lines of antibacterial compositions subdividing said surface into a multiplicity of individual test areas, said antibacterial compositions serving as an effective barrier for preventing interference between adjacent test areas.

While many types of antibacterial compositions can be used in the present invention a very simple and readily available source are the aniline dyes such as Brilliant Green which can be incorporated into an ink of a pen or dry marker.

BRIEF DESCRIPTION OF THE DRAWINGS

The FIGURE shows a support having test areas resulting from drawing lines with a permanent marker to form parallel channels.

DESCRIPTION OF THE PREFERRED EMBODIMENTS

In a preferred embodiment according to this aspect of the invention said lines are drawn on a sheet of bilbulous cellulose which is then impregnated with liquid bacterial culture. Preferably in this embodiment said testing surface is supported on a solidifying growth medium such as one containing agar-agar.

The invention will now be described in connection with certain preferred embodiments in the following examples and with reference to the following illustrative figure so that aspects thereof may be more fully understood and appreciated. It is not intended, however, to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

A pen, containing Brilliant Green as a component of the ink, is used for drawing a grid (10 mm×10 mm squares) on a sheet of filter paper. The sheet is cut into 60 mm×60 mm pads. Thus each pad will conveniently fit into a Petri dish. The pads are sterilized, e.g., by dry heat or in an autoclave, and then placed on the surface of a freshly seeded agar plate. The ink prevents growth along the lines of the grid since it contains Brilliant Green, a powerful antibacterial dye. If a "permanent"

marker is used as the pen, the ink will not diffuse since it is not soluble in water and the inhibition zones will correspond precisely to the lines drawn on the grid. Furthermore, such lines can thus be made to provide a barrier to the diffusion of water soluble solutes across the grid. Thus each little square in the grid will provide a distinct and separate test area on the agar.

While the Pateri dish is the commonly available vessel, any other form of solid culture with a conveniently accessible surface can be used. Similarly, while dyes inhibitory to bacteria are convenient to use, the invention is not restricted to colored substances. Obviously a dye can be added to a colorless inhibitor, if desired, to facilitate preparation of grid-pad(s). The choice of inhibitor will depend on the sensitivity of the bacterial test strain. A combination of non-diffusing inhibitors may be preferred in some tests.

Limited diffusion of inhibitory components of the grid may have an advantage. For example, a synergistic effect of such components with antibacterials which the test is used to detect, may improve the sensitivity of the test. On the other hand, undesirable effects of such a limited diffusion on very sensitive test strains can be controlled by including small amounts of protein in the medium or in the test area.

It will be realized that for many purposes a plate with a 25-square grid will be equivalent to 25 plates, providing, e.g. discreet areas for testing the sterility of 25 different specimens. Similarly it will allow rapid estimates of bacterial counts by the conventional methods of varying sample sizes, but with economy that may be important in screening, e.g., for bacteriuria.

EXAMPLE 2

The procedure of Example 1 is repeated, however, instead of seeding the plate, the grid-pad is impregnated with the desired bacterial culture. The pad is then placed on the unseeded plate or on any other solid medium, gelled or impregnated. For short term incubations the medium in the grid-pad(s) will suffice, in which case the plate will only be required to provide protection against contamination and against drying out.

EXAMPLE 3

The grid-pad suggests a new approach to the sensitivity testing which is a major routine in all hospital laboratories as follows:

Instead of 6 antibiotic discs, a plain grid-strip consisting of 6 test-areas and 6 grid-strips impregnated with the 6 antibiotics, are provided. The strips are placed side-by-side and 6 cultures to be tested are streaked across. Thus one plate serves to replace six plates. Furthermore, the strips will contain a non-diffusible color indicator of metabolic activity.

A distinct change in color in the antibiotic-free area appears within 3-4 hours in most strains. The change thus provides a reference for assessing the sensitivity profile of the corresponding strain.

The savings in steps, labor, plates and time combine to provide a superior sensitivity testing method.

For large-scale screening the format can be further simplified. Thus, each plate, or a tray of the appropriate dimension, may include a single compound of interest, e.g., an antibiotic or a sugar, in the medium or in the grid, so that dozens of specimens can be simultaneously tested.

Similar kits can be constructed for testing biochemical traits essential for the identification of a microorganism. This can be illustrated by the examples of carbohydrate fermentation profile as a diagnostic aid in identification. It is easy to see that grid-strips can be impregnated with a series of sugars and a pH indicator to provide a kit otherwise identical to that described above. With a heavy inoculum the test can be very rapid.

For very rapid tests, including the example above, the medium in the grid will suffice and the protection afforded by the vessel will not be needed. This will allow wide departures from standard formats, e.g. use of sheets in plastic files.

A solid growth medium, e.g. nutrient agar, can absorb ink and hence can be imprinted with a grid. For practical reasons, the imprinting may preferably involve a template, e.g. a plain paper disc cut to fit a Petri dish and imprinted with the desired grid. The disc is placed at the bottom of a Petri dish into which the agar is subsequently poured. After gelling and having absorbed the print, the molded agar can be easily lifted. Both faces of the agar can thus be used. This format is uniquely suited for maintaining complete physical separation between, e.g. bacteria seeded on one face and reagents applied to the other face. Similarly, two different grids can be applied to the two faces, since the bacteria may be incorporated in the agar. Thus a variety of superimposed effects can be directly observed.

EXAMPLE 4

Combined channels for drug sensitivity testing

A permanent marker, containing Brilliant Green as a component of the ink, is used for drawing 10 mm wide parallel channels on a sheet of filter paper. Such channels are insulated against cross-contamination by solute or by bacteria. Thus each channel provides a distinct and separate test area when the sheet is cut into convenient size (e.g. 80 mm $\times$ 60 mm) pads.

Furthermore, when 2 (or more) "channeled pads" are aligned and brought in wet contact, the combined test areas thus created will allow diffusion between the corresponding super imposed channels, without risk of contamination of adjacent channels.

The unique advantages of such combined test areas are illustrated by the following application. A specimen of urine is tested for the presence of viable bacteria and for their susceptibility to 6 selected antibiotics. The bacteria are collected by centrifugation or filtration, and suspended in 0.3 ml of unbuffered nutrient broth containing glucose and a pH indicator (BIG). The suspension is placed in a trough from which it is soaked up by one of the channeled pads. By this angle operation the bacterial suspension is equally subdivided among the 8 channels, with the bacteria concentrated at the bottom of each channel. Furthermore, this "culture pad" will support the growth of such bacteria except where inhibited. The culture pad is brought in contact with an "antibiotic pad", impregnated with 6 antibiotics, one per channel, and providing a "growth control" channel which is not impregnated and an "inhibition control" channel impregnated with a disinfectant. A third pad, soaked in BIG provides a reserve of medium and moisture for more prolonged incubations. In most cases, results can be read within 2 hours (at 37° C.), namely, when a distinct change in color is noted in the "growth control channel" while the "inhibition control" remains unchanged. The effect of other antibiotics is then assessed by visual comparison with the controls.

In a preferred embodiment the 3 pads are prealigned and stapled together between transparent plastic covers to form a "booklet" which is stored in a transparent plastic envelope until use. Simultaneous soaking of 'culture pads' and of 'medium pads' (soaked in a BIG) is carried out from the respective troughs and the booklet is replaced in the envelope which is then sealed and incubated. In this embodiment handling is minimal, no incubator is needed (a vest pocket has been successfully used) and results are read at a glance.

EXAMPLE 5

Testing for the presence and properties of β-lactamase in mastitic milk

A sheet of Whatman No. 3 filter paper pad is impregnated with a starch-iodine mixture and, after drying it cut into a rectangular strip 2, as shown in the attached figure, having provided at an end 3 thereof two oppositely extended triangular extensions 4, 6.

Using a permanent marker (Pelikan) a meandering switchback line 8 is drawn, which line is water insoluble and which has antibacterial properties due to the aniline dye therein. As shown said switchback line 8 is drawn to define two pairs of closed end channels 10, 12 and 14, 16 extending substantially parallel to each other, the open end of each pair facing in opposite directions and being open to fluid diffusion of solutions deposited on extensions 4, 6 respectively, in the direction of the arrows indicated thereon.

Spots of benzylpenicillin 18, 20 are deposited at the mouths of channels 10 and 14 and spots of cloxacillin 22, 24 are deposited at the mouths of channels 12 and 16, respectively.

These β-lactams are potential substrates of β-lactamase. The products of β-lactamase reaction will remove iodine from the dark starch-iodine complex and thus cause decolorization of the test area.

The test is then carried out by dipping extension 4 in clean control milk and dipping extension 6 in the specimen milk to be tested. Alternatively, one or more drops of each type of milk could be dripped onto the respective extension whereafter both samples diffuse into the respective channels 10, 12, 14 16.

If the specimen contains β-lactamase, its activity against benzylpenicillin and cloxacillin is assessed directly by observing decolorization of the respective test areas as compared to adjacent control areas.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A solid support for bacterial culture having an absorbent testing surface for solid phase bacteriological testing comprising: a plurality of essentially non-diffusing lines of an essentially water-insoluble antibacterial composition comprising an aniline dye inhibitory to bacteria subdividing said surface into a multiplicity of individual adjacent test areas, said antibacterial composition serving as an effective barrier for preventing interference between adjacent test areas; wherein said testing surface includes a bacterial growth medium or said surface is supported on a solidifying bacterial growth medium.

2. A solid support for bacterial culture having an absorbent testing surface for solid phase bacteriological testing according to claim 1, wherein said lines form an intersecting array.

3. A solid support for bacterial culture having an absorbent testing surface for solid phase bacteriological testing, according to claim 1, wherein said antibacterial composition comprises Brilliant Green.

4. A solid support for bacterial culture having an absorbent testing surface for solid phase bacteriological testing, according to claim 3, wherein said composition is an ink.

5. A solid support for bacterial culture having an absorbent testing surface for solid phase bacteriological testing according to claim 1, wherein said growth medium contains agar-agar.

6. A solid support for bacterial culture having an absorbent testing surface for solid phase bacteriological testing, according to claim 1, wherein said testing surface is supported on an absorbent support material.

7. A solid support for bacterial culture having an absorbent testing surface for solid phase bacteriological testing comprising: a plurality of essentially non-diffusing lines of an essentially water-insoluble antibacterial composition comprising an aniline dye inhibitory to bacteria subdividing said surface into a multiplicity of individual adjacent test areas, said antibacterial composition serving as an effective barrier for preventing interference between adjacent test areas, wherein said lines are formed on a sheet of bibulous cellulose and wherein the individual areas are impregnated with bacterial culture.

* * * * *